United States Patent [19]

Schwartz

[11] Patent Number: 4,647,671

[45] Date of Patent: Mar. 3, 1987

[54] CLEAVABLE CROSS-LINKING REAGENT

[76] Inventor: Martin A. Schwartz, 19 Bellis Cir., Cambridge, Mass. 02140

[21] Appl. No.: 694,698

[22] Filed: Jan. 25, 1985

[51] Int. Cl.[4] ............................................ C07D 207/452
[52] U.S. Cl. ...................................... 548/545; 424/1.1
[58] Field of Search .......................................... 548/545

[56] References Cited

PUBLICATIONS

Chong et al., J. Biol. Chem., vol. 256, 5064–5070, (1981).
Schwartz et al., J. Biol. Chem., vol. 257, 2343–2349, (1982).
Denny et al., Proc. Natl. Acad. Sci., USA, vol. 81, 5286–5290, (1984).
Schwartz, J. Cell. Biol., vol. 99, pt 2, (Oct. 1984).

Primary Examiner—Richard L. Raymond
Assistant Examiner—D. B. Springer

[57] ABSTRACT

An alkali-cleavable heterobifunctional cross-linking analytical reagent is provided in the form of a compound having the structure (2-hydroxy-5-azidobenzoyl)-NH—$R_1$—
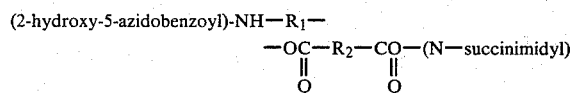

in which $R_1$ and $R_2$ is each an alkylene group having from 2 to 4 carbon atoms.

8 Claims, No Drawings

CLEAVABLE CROSS-LINKING REAGENT

This invention was made with Government support and the Government has certain rights in the invention.

This invention relates to an alkali-cleavable heterobifunctional cross-linking analytical reagent adapted to be radiolabelled, and to a radiolabel-transfer cross-linking analytical reagent.

It has previously been proposed to provide as a cleavable heterobifunctional cross-linking reagent N-(4-azidobenzoyl-glycyl)-S-(2-thiopyridyl)-cysteine in which the glycyl group is radiolabeled, as described by Chong et al., J. Biol. Chem., Vol. 256, 5064–5070 (1981). It has also been proposed to provide a radiolabeled cleavable heterobifunctional cross-linking reagent in the form of 3-[(2-nitro-4-azidophenyl)-2-aminoethyldithio]-N-succinimidyl propionate as described by Schwartz et al., J. Biol. Chem., Vol. 257, 2343–2349 (1982). In addition, a radiolabelled cleavable heterobifunctional cross linking reagent has been described in Denny et al., Proc. Natl. Acad. Sci. USA, Vol. 81, 5286–5290 (1984). While all three of these cross-linking reagents are useful for identifying proteins by attaching a radioactive label thereto, the radioactive label must be inserted in the reagent in each case during synthesis of the reagent so that the reagent has only limited storage life and reguires special care in storage and handling. Furthermore, both of the first two of these reagents contain a disulfide group as the cleavage site and hence are subject to possible disulfide interchange under conditions where the concentration of free sulfhydryl groups is high, as for example within the cytoplasm, so that their use for identification of cytoplasmic proteins is precluded. The third of these reagents is cleavable with dithionite (hydrosulfite) and exhibits low efficiency as a label transfer reagent.

The present invention provides compounds having the structure

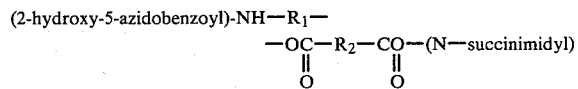

in which $R_1$ and $R_2$ is each an alkylene group having from 1 to 4 carbon atoms. These compounds are stable and can readily be stored for long periods of time at room temperature. They can be radiolabeled in the 2-hydroxy-5-azidobenzoyl group shortly before use by conventional procedures, for example by iodinating with an iodine isotope such as $^{125}I$ using the chloramine-T method. The compounds, whether radiolabeled or not, are stable both in dry solid form and in solution in organic solvents such as chloroform and tetrahydrofuran in the dark. In the dark or in red light, the succinimidyl group reacts with an amino group of a protein to form an amide bond. This compound is stable in agueous media at a pH from 4–9 but can rapidly be cleaved at the ester linkage above about pH 11; at pH 12, hydrolytic cleavage of the ester linkage is complete in approximately one minute at room temperature. In this compound, after reaction with protein, upon exposure to light of appropriate wave length the azido group is converted to a reactive nitrene capable of reacting with a variety of sites on proteins, polypeptides, or nucleic acids to form a cross-linked complex. The photolyzed cross-linked complex hydrolyzes slowly at the ester linkage at neutral pH thereby transferring the radiolabel from the initial protein to an adjacent molecule. Hydrolysis can be accelerated by raising the pH to a value above pH 11, as in the unphotolyzed compound.

The reagent of the present invention is used by reacting it in the dark with a desired purified protein to bond the reagent to the protein, then inserting the product into a biological system, after which the system is subjected to photolysis to form cross-links through the activated azido group to adjacent components of the system, and finally cleaving the cross-links by raising the pH to leave the radiolabeled moiety of the reagent attached to the last component, which can thus be identified and isolated by conventional procedures.

The following example will serve to illustrate more fully the nature of the present invention without acting as a limitation upon its scope.

EXAMPLE

The compound 1-(N-(2-hydroxy-5-azidobenzoyl)-2-aminoethyl)-4-(N-hydroxysuccinimidyl)-succinate (HAHS) was prepared by the following procedure, all of the steps being carried out in red light.

1. Preparation of 5-azido-2-hydroxybenzoic acid

The compound 5-amino salicylic acid (10.0 g, 0.065 mol) was dissolved in 150 ml 8% (vol/vol) HCl in water and stirred on ice. Sodium nitrite (5.50 g, 0.080 mol) in 10 ml water was added slowly and then stirred for 30 min. Hydroxylamine hydrochloride (5.6 g, 0.081 mol) in 10 ml water was added, and the reaction mixture was poured into 300 ml of a 15% (wt/vol) solution of sodium carbonate. After 20 min the mixture was filtered, the filtrate acidified to pH 2 with conc. HCl, and the precipitate collected by filtration. The product was recrystallized twice from acetonitrile and ddried in vacuo. Yield: 4.45 g (38%). Analysis by thin layer chromatography on silica gel eluted with ethyl acetate showed the product to be about 95% pure. IR spectrum: strong peaks at 2100 and 1660 cm-1 corresponding to the azide and carboxylic acid groups respectively.

2. Preparation of ethanolamine 5-azido-2-hydroxy benzoic amide

The compound prepared in Step 1 above (1.00 g, 5.59 mmol) was dissolved in 8 ml tetrahydrofuran, 0.68 ml thionyl chloride was added, and the mixture incubated at room temperature overnight. It was evaporated to dryness, redissolved in tetrahydrofuran, and 0.82 ml ethanolamine in 4 ml tetrahydrofuran added slowly with stirring. After an additional 5 min, the solution was extracted 3x with 10 ml 0.1 M pH 7.0 sodium phosphate, 2M NaCl, dried over magnesium sulfate, filtered, and evaporated to dryness. The product was dissolved in ethyl acetate and run through a small silicic acid column to remove a small amount of highly colored contaminant. Thin layer chromatography on silica gel eluted with ethyl acetate showed that the amide (Rf. 0.45) was slightly contaminated with impurities a rf. 0.01 and 0.67, but these came to less than 10%. The fast running component could be removed by dissolving the product in methanol and extracting with hexane. IR spectrum: strong peaks at 2070 and 1635 cm-1 correspond to the azido and amide groups respectively. UV spectrum: absorbance maximum at 322 nm, E=13000 M-1 cm-1.

3. Synthesis of 1-(N-(2-hydroxyl-5-azidobenzoyl)-2-aminoethyl)-4-(N-hydroxysuccinimidyl)-succinate, or HAHS.

Succinyl chloride (0.10 ml, 0.88 mmol) and N,N-dimethyl aniline were dissolved in 1.0 ml tetrahydrofuran. N-hydroxysuccinimide (0.060 g, 0.52 mmol) dissolved in 1 ml tetrahydrofuran was added and the reaction incubated 30 min at room temperature. Then the compound prepared in Step 2 above (0.10 g, 0.45 mmol) in 1 ml THF was added, and the mixture incubated a further 30 min at room temperature. The mixture was evaporated to a thick oil, dissolved in chloroform, and passed through a 5 ml silicic acid column in chloroform. The fractions containing the product were pooled, evaporated, redissolved in chloroform, and rechromatographed on a Waters HPLC silicic acid column in chloroform. This yielded a small amount of highly purified HAHS which migrated as a single peak on TLC in ethyl acetate. It was filtered through a 0.45 micron nylon filter and stored in chloroform in the dark, at $-20°$ C. IR: strong peaks at 2070, corresponding to the azido group, and at 1635, 1745, 1780 and 1810 cm-1, corresponding to the amide, ester, and succinimide ester carbonyl moieties. The product was stable when stored in the dark for extended periods of time.

4. Iodination of HAHS

To a polypropylene micro test tube were added in rapid succession with mixing, 0.05 to 1.0 mCi iodine-125 in NaOH, an equal volume of 2 mg/ml chloramine T in 0.1 M pH 7.0 sodium phosphate, 0.2–2.0 uL 1 mg/ml HAHS in acetone, and 1 uL 1 M sodium thiosulfate. At this point, the iodination of HAHS may be assessed either by extraction into ether to separate the iodinated reagent from the free sodium iodide, or by thin layer chromatography. 40 to 60% of the starting radioactivity becomes extractable into ether after the reaction (compared to less than 5% if HAHS or chloramine T are omitted), and 90% of this cochromatographs with unlabeled HAHS on silica gel.

The use of the labeled HAHS as a label transfer reagent is illustrated by the following procedure. Immediately after iodination, protein at greater than 1 mg/ml in pH 7-8 sodium phosphate is added to the reaction mixture and incubated 30 min on ice. The protein is separated from unreacted reagent and from free iodine by gel filtration on Biogel P-2 or Sephadex G-25. 5–20% of the total starting radioactivity, or 10–40% of the radiolabeled HAHS becomes associated with the protein under these conditions, and is 99% TCA precipitable. The association of radioactivity with the protein is completely blocked by including 20 mM ethanolamine in the protein solution.

After labeling, the protein derivative can be added back into the desired system in proximity to other proteins to be identified. The system can be subjected to photolysis and the azido containing moiety after photolysis reacts with a protein in the system. Cleavage of the ester linkage occurs spontaneously after photolysis, although much more slowly than when alkali is added to raise the pH. Photolysis can be carried out at room temperature by exposing to light for 30 sec. using a 100 watt long wave UV lamp with maximum output at 360 nm and a filter to cut off radiation below 300 nm. Label transfer is complete after about 10 seconds.

When HAHS on protein A was bound to IgG and photolyzed, 27% of the label was transferred to the IgG heavy chain. This is exceptionally efficient for a photochemical reaction.

When noninteracting proteins were added, they received lower amounts of label. IgG heavy chain was preferred over ovalbumin and RNase by about 200:1. The preference for IgG over BSA was only 45:1.

In summary, HAHS provides a comparatively easy reagent for analyzing the interactions of proteins. It is chemically compatible with the intracellular environment and can transfer label from an initial protein to its neighbors with high efficiency. It is synthesized from inexpensive starting materials in three steps, and can be stored as an unlabeled precursor, then radiolabeled e.g. by iodination immediately before use. It can be cleaved under conditions which do not affect normal esters, or can cleave spontaneously after photolysis.

Similar results can be obtained in the case of corresponding compounds containing aminopropyl or aminobutyl groups instead of aminoethyl, and containing malonate adipate or glutarate moieties instead of succinate.

What is claimed is:

1. A compound having the structure

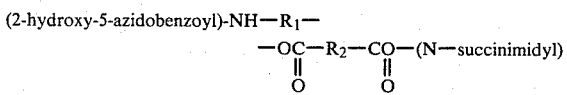

in which $R_1$ and $R_2$, is each an alkylene group having from 1 to 4 carbon atoms.

2. A compound as claimed in claim 1 in which $R_1$ contains two carbon atoms.

3. A compound as claimed in claim 1 in which $R_2$, contains two carbon atoms.

4. A compound as claimed in claim 1 which is 1-(N-(2-hydroxy-5-azidobenzoyl)-2-aminoethyl)-4-(N-hydroxysuccinimidyl) -succinate.

5. A compound as claimed in claim 1 which is radiolabeled with iodine isotope.

6. A compound as claimed in claim 2 which is radiolabeled with iodine isotope.

7. A compound as claimed in claim 3 which is radiolabeled with iodine isotope.

8. A compound as claimed in claim 4 which is radiolabeled with iodine isotope.

* * * * *

UNITED STATES PATENT AND TRADEMARK OFFICE
CERTIFICATE OF CORRECTION

PATENT NO. : 4,647,671
DATED : March 3, 1987
INVENTOR(S) : Martin A. Schwartz

It is certified that error appears in the above-identified patent and that said Letters Patent are hereby corrected as shown below:

Column 1, line 21, "cross linking" should be hyphenated;

Column 1, line 27, "requires" is misspelled;

Column 1, line 57, "aqueous" is misspelled;

Column 2, line 61, "a" should be --at--.

Signed and Sealed this

Thirtieth Day of June, 1987

Attest:

DONALD J. QUIGG

Attesting Officer

Commissioner of Patents and Trademarks